US008314136B1

United States Patent
DeLack

(10) Patent No.: US 8,314,136 B1
(45) Date of Patent: *Nov. 20, 2012

(54) METHOD FOR TREATMENT OF ALZHEIMER'S DISEASE AND AUTISM SPECTRUM DISORDERS

(75) Inventor: Elaine A. DeLack, Stanwood, WA (US)

(73) Assignee: MedDEV, Inc., Stanwood, WA (US)

( * ) Notice: Subject to any disclaimer, the term of this patent is extended or adjusted under 35 U.S.C. 154(b) by 366 days.

This patent is subject to a terminal disclaimer.

(21) Appl. No.: 12/660,257

(22) Filed: Feb. 23, 2010

Related U.S. Application Data

(63) Continuation-in-part of application No. 11/805,624, filed on May 23, 2007, now Pat. No. 7,666,893.

(60) Provisional application No. 60/808,032, filed on May 23, 2006.

(51) Int. Cl.
  *A01N 43/50* (2006.01)
  *A61K 31/415* (2006.01)

(52) U.S. Cl. .................. 514/400; 548/334.5

(58) Field of Classification Search .......... 514/400; 548/334.5
See application file for complete search history.

(56) References Cited

U.S. PATENT DOCUMENTS

| 4,055,573 | A  | 10/1977 | Mendelson |
| 6,277,402 | B1 | 8/2001  | DeLack |
| 6,359,145 | B1 | 3/2002  | Terasaka et al. |
| 6,426,360 | B1 | 7/2002  | Weier et al. |
| 6,596,738 | B1 | 7/2003  | Terasaka et al. |
| 6,617,324 | B1 | 9/2003  | Naraian et al. |

FOREIGN PATENT DOCUMENTS

WO    WO 03063781 A2 *  8/2003

OTHER PUBLICATIONS

Kubo et. al., Journal of Agricultural and Food Chemistry, 2002, American Chemical Society, vol. 50, pp. 6692-6696.*
Huffman et. al., Bioorganic and Medicinal Chemistry, 2005, Elsevier, vol. 13, pp. 89-112.*
Watson et. al., Journal of the Neurological Sciences, 2006, Elsevier, vol. 245, pp. 21-33.*
Alberdi et al. (2009), Amyloid B oligomers induce Ca2+ dysregulation and neuronal dealth through activation of . . . Cell Calcium, pp. 1-9.
Alcazar et al. (1998). Induction of apoptosis by cerebrospinal fluid from patients with primary-rpogressive multiple sclersos . . . Neuroscience Letters, 255, pp. 49-54.
Aulkemeyer et al. (2000). The small sodium-channel blocking factor in cerebrospinal fluid of multiple sclerosis patents . . . Journal of neurological Science, 172(1), pp. 49-54.
Baslow, M.H. (1998). Function of the N-acetyl-L-histidine system in the vertebrate eye. Journal of Molecular Neuroscience, 10(3), pp. 193-208.
Behan et al. (2002). The pathogenesis of multiple sclerosis revisted. J R College of physicians Edinb, 32, pp. 244-265.
Blaustein, M.P. (1975). Effects of potassum, veratridine, and scorpion venom on calcium accumulation and transmitte . . . Journal of Physiology, 247*3), pp. 617-655.
Carvounis, C.P. (1985). Importance of amino acids on vasopressin-stimulated water flow. Journal of Clinical Investigation, 76(2), pp. 779-788.
Chua et al. (2002). MRI findings in osmotic myelinolysis. Clinical Radiology, 57(9), pp. 800-806.
Cid et al. (2002). Neronal apoptosis induced by cerebrospinal fluid from multiple sclerosis patients . . . Journal of Neurological Science, 193(2), pp. 103-109.
Davies et al. (1988). Hyposomolarity induces an increase of extracellular N-acetylaspartate concentration in the rat striatum. neurochemical Research, 2393), pp. 1021-1025.
Davis et al. (2002). Glial fibrillary acidic protein in late life major depressive disorder . . . Journal of neurology Neurosurgery Psychiatry, 73(5), pp. 556-560.
Fields, R.D. (2004). The other half of the brain: Mounting evidence suggests that glial cells, overlooked for half a century, may . . . Scientific America, pp. 54-61.
Gehl et al. (2004). Biosynthesis of NAAG by an enzyme-mediated process in rat central nervous system neurons and glia. Journal of Neurochemistry, 90(4), pp. 989-997.
Hertz et al. (2004). Astrocytic adrenoceptors: A major drug target in neurological and psychiatric . . . Current Drug Targets CNS Neorological Disorders, 3(3), pp. 239-267.
Huang et al. (2000). Transport of N-acetylasparate by the Na(+)-dependent high affinity dicarboxylate . . . Journal of Pharmacology Experimental Therapies, 295(1), pp. 392-403.
Jesse et al. (2009). Glial Fibrillary Acidic Protein and Protein S-100B: Different Concentration Pattern of . . . Journal of Alzheimer's Disease, 17, pp. 541-551.
Kashon et al. (2004). Associations of cortical astrogliosis with congnitive performation and dementia . . . Journal of Alzheimer's Disease, 6(6), pp. 595-604; discussion 673-681.
Kiline et al. (2002). Osmotic myelinolysis in a normonatremic patient. Acta Nerology Belgium, 102(2), pp. 87-89.
Kleinhans et al. (2007). N-acetyl aspartate in autism specrum disorders: Regional effects . . . Science Direct, pp. 85-97.

(Continued)

*Primary Examiner* — Sreeni Padmanabhan
*Assistant Examiner* — Sarah Pihonak
(74) *Attorney, Agent, or Firm* — Todd N. Hathaway

(57) ABSTRACT

A method for treating Alzheimer's Disease (AD) or Autism Spectrum Disorder (ASD) by administering at least one alky ester of imidazolecarboxylc acid, preferably methyl 4-imidazolecarboxylate. It is hypothesized that the treatment counters AD/ASD by maintaining the intracellular/extracellular osmolyte gradient in the central nervous system (CNS) within a substantially normal range. The methyl 4-imidazolecarboxylate may be administered orally, by inhaler, by injection or by transdermal application. When administered by transdermal application, the dosage range may be from about 0.01 mcg per day to about 3.0 mcg per day, preferably from about 0.1 mcg per day to about 0.3 mcg per day.

5 Claims, No Drawings

OTHER PUBLICATIONS

Koller et al. (1996). Cerebrospinal fluid from multiple sclerosis patients inactivates neuronal Na+ current. Brain, 119(Pt 2), pp. 457-463.

Mews et al. (1998). Oligodendrocyte and axon pathology in client silent multiple sclerosis lesions. Multiple Sclerosis Journal, 4(2), pp. 55-62.

Oliveira et al. (2004). Alterations in the central vasopressin and oxytocin axis after lesion of a brina osmotic sensory region. Brain Research Bulletin, 63(6), pp. 515-520.

Pastural et a. (2009). Novel plasma phospholipid biomarkers of autism: Mitochndrial dysfunction . . . 81, pp. 253-264.

Perea et al. (2005). Synaptic regulation of the astrocyte calcium signal. Journal of Neurl Transmission, 112(1), pp. 127-135.

Pilatus et al. (2009). Conversion to dementia in mold congnitive impariment is associated with decline of N-actylaspartate . . . Psychiatry Research: Neuroimaging, 173, pp. 107.

Ramsey et al. (1984). The defence of plasma osmolaity. Journal of Physiology (Paris), 79(6), pp. 416-420.

Resengren et al. (1992). A sensitive ELISA for glial fibrillary acidid protein . . . Journal of Neuroscience Methods, 44, pp. 113-119.

Sager et al. (1999). Astroglia contain a specific transport mechanism for N-acetyl-L-aspartate. Journal of Neurochemistry, 73(2), pp. 807-811.

Schiepers et al. (1997). Positron emission tomography, magnetic resonance imaging and proton NMR . . . Multiple Sclerosis Journal, 3(1), pp. 8-17.

Sharma et al. (1992). Histamine modules heat stress-induced chantes in blood-brain barrier permeability, cerebral bloos flow . . . Neuroscience, 50(2), pp. 445-454.

Simard et al. (2004). The neurobiology of glia in the context of water and ion homeostatis. Neuroscience, 129(4), pp. 877-896.

Tateishi et al. (2006). S100B: astrocyte specific protein. Nihon Schinkei Seishin Yakurigaku Zassi, 26(1), pp. 6-11.

Vivekanandhan et al. (2005). Adenosine deaminase and 5-nucleotidas activities in peripheral blood T cells . . . Neurochemistry Research, 30(4), pp. 453-456.

Williamson et al. (1988). Clacium-dependent release of N-actylaspartylglutamate from retinal neurons upon depolarization. Brain Research, 475(1), pp. 151-155.

Alzheimer's Disease Fact Sheet. www.nia.nih.gov., (Nov. 2008).

* cited by examiner

METHOD FOR TREATMENT OF ALZHEIMER'S DISEASE AND AUTISM SPECTRUM DISORDERS

RELATED APPLICATIONS

This application is a Continuation-In-Part of U.S. Non-Provisional application Ser. No. 11/805,624 filed May 23, 2007 now U.S. Pat. No. 7,666,893, which claims the benefit of U.S. Provisional Patent Application Ser. No. 60/808,032 filed May 23, 2006.

BACKGROUND OF THE INVENTION a. Field of the Invention

The present invention relates generally to the methods for the treatment of Alzheimer's Disease (AD) and Autism Spectrum Disorder (ASD) and more particularly to methods for treatment of AD and ASD by administration of an alkyl ester of imidazole carboxylic acid in order to maintain the intracellular/extracellular osmolyte gradient in the central nervous system (CNS).

b. Background

Alzheimer's Disease (AD) is a neurodegenerative disease that slowly destroys memory and thinking skills, and eventually impairs the ability to carry out simple activities of daily living. The first symptoms of AD which are memory loss, language problems, and unpredictable behavior generally appear after age 60. It is estimated that 2.4 to 4.5 million Americans are living with AD (www.nia.nih.gov/Alzheimers/Publications/adfact.htm)

The root cause of AD is unknown but genetic and environmental factors are suspected. The disease progresses over time, presenting in the early stage with short-term memory and cognitive difficulties e.g. repeating questions, poor judgment, and mood and personality changes. The disease then progresses to moderate AD in which parts of the brain are affected that control language, reasoning, sensory processing and conscious thought. Often by this stage of AD, people withdraw from social interaction. In the final stage of AD, people are unable to communicate and they become completely dependent on others for their care.

The progression of AD is positively correlated with the development of neurofibrillary tangles and amyloid plaques that spread throughout the brain and inversely correlated with loss of neurons.

Four medications are currently approved by the U.S. Food and Drug Administration to treat AD: Donepezil (Aricept®), rivastigmine (Exelon®), galantamine (Razadyne®), and memantine (Namenda®). These drugs work by regulating neurotransmitters and may help to maintain thinking, memory, and language skills for a few months to years, however, they do not change the underlying disease process.

Autism Spectrum Disorder (ASD) has many similar symptoms as Alzheimer's Disease (AD). Like AD, the severity of symptoms of ASD are on a spectrum. Autism Spectrum Disorder, also known as Pervasive Developmental Disorders (PDD), is generally considered to encompass five more particular disorders: Autism; Asperger Syndrome; Rett Syndrome; Childhood Disintegrative Disorder; and Pervasive Developmental Disorder Not Otherwise Specified (atypical autism). Childhood autism, also known as autistic disorder or infantile autism, is a neuro-developmental condition that is characterized by impairment in social interaction, impairment in communication and restricted or stereotyped patterns of behavior and interest usually manifested before the age of 3 years. Common symptoms of ASD include: impaired social and communication skills (verbal and nonverbal); delayed or unusual speech patterns; hyper or hypo sensitivity to light, sound, crowd and other external stimulation; some degree of fine and gross motor difficulty; repetitive behaviors and ritualized activities; aloofness or disengagement with surrounding environment, inability to handle stress or change in routine or environment; some patients have a degree of mental retardation and one in four develop seizures. The severity of these symptoms is very individualized in persons diagnosed with ASD.

The incidence of ASD has increased dramatically over the last decade, and today 1 in 100 children are diagnosed as having ASD. The root cause of ASD still eludes the medical community, but several factors have been implicated such as hereditary, heavy metal toxicity, vaccinations, exposure to high amounts of Pitocin (oxytocin) and/or opioids during birth, food allergies, and vitamin and mineral deficiencies.

Currently only one medication, risperidone, has been approved by the FDA for the symptomatic treatment of irritability in autistic children. Several medications have been used "off-label" to help lessen some of the symptoms associated with ASD, but with limited effectiveness. Some of these medications are antipsychotic medications, antidepressants such as Selective Serotonin Reuptake Inhibitors (SSRIs), alpha adrenergic agonists, anticonvulsants, and stimulants such as Ritalin or Provigil. (http://autism.about.com/od/treatmentoptions/p/drugtreatments.htm).

Accordingly, there exists a need for a method for treatment of AD and ASD that approaches the fundamental cause of the disorders in a more direct manner than prior treatments and therefore provides treatment with a greater degree of effectiveness.

SUMMARY OF INVENTION

The present invention addresses the problems cited above, and is a method for treating Alzheimer's Disease and Autism Spectrum Disorders by addressing the intracellular/extracellular osmolyte gradient in the central nervous system.

Broadly the method comprises the step of administering to a patient suffering from Alzheimer's Disease or Autism Spectrum Disorder an effective amount of at least one alkyl ester of imidazole carboxylic acid. Preferably, the at least one alkyl ester of imidazole carboxylic acid is administered in an amount sufficient to maintain the intracellular/extracellular osmolyte gradient in the CNS within a substantially normal range.

The at least one alkyl ester of imidazole carboxylic acid may be methyl 4-imidazolecarboxylate. The methyl 4-imidazolecarboxylate may be administered orally, by inhaler, by injection, by transdermal application or combinations thereof.

When administered by transdermal application, the dosage range of the methyl 4-imidazolecarboxylate may be from about 0.0 mcg to about 3.0 mcg per day, with a preferred dosage range being from about 0.1 mcg to about 0.3 mcg per day. In a preferred embodiment the methyl 4-imidazolecarboxylate may be administered by transdermal application in an amount of about 0.2 mcg on a schedule of one day on and two days off.

DETAILED DESCRIPTION

The present invention provides a method for treatment of Alzheimer's Disease and Autism Spectrum Disorders by the administration of one or more alkyl esters of imidazole carboxylic acid, preferably methyl 4-imidazolecarboxylate, in amounts sufficient to maintain the intracellular/extracellular osmolyte gradient in the CNS.

a. Hypothesis and Mechanism

Neuron loss is associated with both Alzheimer's Disease and Autism Spectrum Disorder.

As part of the present invention, it is non-bindingly hypothesized that this phenomenon results at least in part from decreased synthesis of the histidine derivatives, specifically the imidazole ring molecule that is methylated on the side-chain—i.e. methyl 4-imidazolecarboxylate—by the neurons and oligodendrocytes, resulting in an impaired intracellular/extracellular osmolyte gradient.

Methyl 4-imidazolecarboxylate has the following molecular structure:

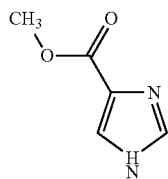

The methyl ester group (—COCH3) is responsible for creating the high-density water networking necessary to maintain the intracellular/extracellular osmolyte gradient.

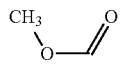

In this functional group, the oxygen atoms are in closer proximity than what normally occurs in bulk water. This creates a higher-density water clustering around these groups. (Water molecules hydrogen-bonded to these oxygens are closer together than they would be in bulk water.)

As part of the present invention, it is hypothesized that the decreased synthesis of the histidine derivatives, in particular decreased synthesis of the methyl ester of imidazole carboxylic acid (i.e. methyl 4-imidazolecarboxylate) by the neurons and oligodendrocytes results in an impaired intracellular/extracellular osmolyte gradient. This results in failure of the high-density water network forming in the extracellular fluid of the synapse and impedes the accumulation of sodium ions in the extracellular fluid and hinders the initiation of entropy that is necessary for the movement of neurotransmission to the astrocytes. This results in very sluggish to absent neurotransmission via the tripartite synapse system. The deficient formation of the high-density water networking in the extracellular fluid and the deficient concentration of sodium ions in the extracellular fluid causes an efflux of potassium ions into the extracellular fluid which can result in death of the neuronal cell and oligodendroctye. Furthermore, the efflux of potassium ions into the extracellular fluid stimulates the release of glutamate from the astrocytes into the tripartite synapse. Glutamate, a carboxylate synthesized by the astrocytes, creates a high-density water network in the extracellular fluid around the astrocyte and attracts calcium ions to accumulate in the extracellular fluid around the astrocyte. The increased extracellular potassium activates the calcium ion channels in the astroctye membranes resulting in the influx of calcium ions into the astroctye, which results in elevated cytosolic calcium levels in the astroctye. Increased cytosolic calcium stimulates mitosis of astrocytes resulting in gliosis. The increase in the number of astrocytes may result in an increase in the uptake of NAA, resulting in an overall decrease in the NAA levels that has been found in the CNS in Alzheimer's Disease and Autism patients. (Pilatus U. et al, (Jul. 15, 2009) Conversion to dementia in mild cognitive impairment is associated with decline of N-actylaspartate and creatine as revealed by magnetic resonance spectroscopy. *Psychiatry Research,* 173(1), pp. 1-7; Kleinhans N. M. et al, Aug. 8, 2007, N-acetyl aspartate in autism spectrum disorders; regional effects and relathipsion of fMRI activation. *Brain Research,* 1162, pp. 85-97).

Research has shown that glial fibrillary acidic protein (GFAP) is elevated in Alzheimer's Disease and Autism Spectrum Disorders (Jesse S. et al, July, 2009. Glial fibrillary acidic protein and protein S-100B: different concentration pattern of flial proteins in cerebrospinal fluid of patients with Alzheimer's disease and Creutzfeldt-Jakob disease. *Journal of Alzheimer's Disease,* 17(3), pp. 541-551; Rosengren L. E. et al, September, 1992. A sensitive ELISA for glial fibrillary acidic protein: application in CSF of children. *Journal of Neuroscience Methods,* 44(2-3), pp. 113-119). GFAP is reliable indicator of astrogliosis, an overgrowth of astrocytes. The increase in the astrocytes could result in the uptake of N-acetyl-L-aspartate (NAA) and increased production of glutamate resulting in the decreased levels of NAA and increased levels of glutamate that are seen in Alzheimer's Disease and Autism. (Alberdi E. et al, Jan. 8, 2010. *Cell Calcium*; Pastural E. et al, October, 2009. Novel plasma phospholipid biomarkers of autism: mitochondrial dysfunction as putative causative mechanism. *Protaglandins Leukotrienes Essential Fatty Acids,* 81(4), pp. 253-264).

Glutamate is neuroexcitatory and elevated levels can be neurotoxic. The release of glutamate by astrocytes is stimulated by extracellular potassium and the release requires the presence of extracellular calcium and the influx (uptake) of the extracellular calcium (Simard & Nedergaard, 2004. The neurobiology of glia in the context of water and ion homeostatis. *Neuroscience,* 129(4) pp. 877-896). The rate of calcium uptake is increased when the concentration of the potassium is increased. (Blaustein, 1975. Effects of Potassium, Veratridine and Scorpion Venom on Calcium Accumulation and Transmitter Release by Nerve Terminals In Vitro. *Journal of Physiology,* 247, pp 617-655).

Consequently, the present invention seeks to maintain the intracellular/extracellular osmolyte gradient in the CSF of patients suffering from Alzheimer's Disease or Autism Spectrum Disorders by the administration of an alkyl ester of imidazole carboxylic acid; methyl 4-imidazolecarboxylate is generally preferred, however, it is anticipated that other alkyl esters of imidazole carboxylic acid may also be suitable and effective. The treatment composition may be administered by any suitable means, such as orally, or by transdermal application, injection or inhaler, to give just a few examples. Administration by transdermal application is preferable in many applicants, in that it provides significant advantages in terms of ease of use, and more consistent dosage levels. Using methyl 4-imidazolecarboxylate, the dosage range is suitably from about 0.01 mcg to about 3.0 mcg per day, with the preferred dosage range being from about 0.1 mcg to about 0.3 mcg per day.

b. EXAMPLES

The following illustrative examples relate to actual practice of the invention described above in the treatment of Alzheimer's Disease and Autism Spectrum Disorder (ASD).

Example One

A 94-year-old female diagnosed with Alzheimer's Disease. Subject's disease had progressed to the level of moderate Alzheimer's requiring assistance with dressing, toileting, and constant reminding to take her pills. She would attempt to eat non-food objects. She seldom joined in conversation and often her verbal responses were inappropriate. She was incontinent of urine.

Three days after initiating the transdermal application of 0.2 mcg of methyl 4-imidazolecarboxylate on a wearing schedule of one day on and two days off, the subject got up and went to the bathroom on her own and she was continent of urine. She was able to dress herself in the morning and had improved short-term memory.

Fifteen days after initiating the transdermal application of 0.2 mcg of methyl 4-imidazolecarboxylate on a wearing schedule of one day on and two days off, the subject became interested in television programs, became very engaging in conversation and answered questions appropriately and her mood was very pleasant. Improved balance was noted.

After one month of applying the transdermal application of 0.2 mcg of methyl 4-imidazolecarboxylate on a wearing schedule of one day on and two days off, the subject would take all of her pills in the morning without needing reminding to take each pill.

After six weeks of applying the transdermal application of 0.2 mcg of methyl 4-imidazolecarboxylate on a wearing schedule of one day on and two days off, the subject began reading to self and out loud. Subject continues to perform more activities of daily living without constant supervision.

Example Two

A 12-year-old male diagnosed with Autism. Subject was developing normally until age two, and had started developing language, 4 word vocabulary. Then at 2½ years of age he suddenly regressed and lost all verbal and nonverbal communication, lost receptive language, developed skin hypersensitivity to touch and would not wear clothes. He would not interact with his environment and would not interact with others.

The transdermal application of 0.2 mcg of methyl 4-imidazolecarboxylate was applied at night since the subject would remove it during the waking hours. The first day following the first night of application, the aid at school said that the subject had increased concentration and focus at school and good eye contact.

After one week of applying the 0.2 mcg of methyl 4-imidazolecarboxylate transdermally every night, the subject verbalized the words, "I'm hungry" at school and his mother reports hearing many new speech sounds.

The subject continues to make progress wearing the transdermal application of 0.2 mcg of methyl 4-imidazolecarboxylate every night. The subject now seeks out his mother and gives her a hug. He is happy and smiling frequently and playing with his brother. He is keeping his clothes on without requiring constant supervision to do so.

It is to be recognized that various alterations, modifications, and/or additions may be introduced into the constructions and arrangements of parts described above without departing from the spirit or ambit of the present invention as defined by the appended claims.

What is claimed is:

1. A method for treatment of Alzheimer's Disease or Autism Spectrum Disorder, said method comprising the steps of:
   administering to a patient in need thereof an effective amount of methyl 4-imidazolecarboxylate.

2. The method of claim 1, wherein the step of administering an effective amount of methyl 4-imidazolecarboxylate comprises administering methyl 4-imidazolecarboxylate by an application selected from the group consisting of:
   transdermal application;
   oral administration;
   inhaler;
   injection; and
   combinations thereof.

3. The method of claim 1, wherein the step of administering an effective amount of methyl 4-imidazolecarboxylate comprises:
   administering methyl 4-imidazolecarboxylate by transdermal application in a dosage range from about 0.01 mcg per day to about 3.0 mcg per day.

4. The method of claim 1, wherein the step of administering an effective amount of methyl 4-imidazolecarboxylate comprises:
   administering methyl 4-imidazolecarboxylate by transdermal application in a dosage range from about 0.1 mcg per day to about 0.3 mcg per day.

5. The method of claim 1, wherein the step of administering an effective amount of methyl 4-imidazolecarboxylate comprises:
   administering methyl 4-imidazolecarboxylate by transdermal application of about 0.2 mcg on a wearing schedule of one day on and two days off.

* * * * *